US008454639B2

(12) United States Patent
Du et al.

(10) Patent No.: US 8,454,639 B2
(45) Date of Patent: *Jun. 4, 2013

(54) DUAL PROBE WITH FLOATING INNER PROBE

(75) Inventors: Shu Du, Erie, PA (US); Thomas M. Peterson, Erie, PA (US); Tao Song, Erie, PA (US); Geoff Bond, Lakewood, NY (US)

(73) Assignee: Cybersonics, Inc., Erie, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/088,421

(22) Filed: Mar. 24, 2005

(65) Prior Publication Data

US 2005/0209620 A1 Sep. 22, 2005

Related U.S. Application Data

(63) Continuation-in-part of application No. 10/334,426, filed on Dec. 30, 2002, now Pat. No. 6,679,191.

(51) Int. Cl.
*A61B 17/32* (2006.01)

(52) U.S. Cl.
USPC ............................................. 606/169; 604/22

(58) Field of Classification Search
USPC ..................... 606/128, 127, 167–172; 604/22
See application file for complete search history.

(56) References Cited

U.S. PATENT DOCUMENTS

| 4,178,935 | A |   | 12/1979 | Gekhman et al. |
| 4,828,052 | A |   | 5/1989  | Duran et al. |
| 5,160,336 | A |   | 11/1992 | Favre |
| 5,176,677 | A | * | 1/1993  | Wuchinich .................... 606/46 |
| 5,414,673 | A |   | 5/1995  | Scherbatskoy |
| 5,562,169 | A |   | 10/1996 | Barrow |
| 5,582,247 | A |   | 12/1996 | Brett et al. |
| 5,676,213 | A |   | 10/1997 | Auzerais et al. |
| 5,868,756 | A |   | 2/1999  | Henry et al. |
| 5,899,958 | A |   | 5/1999  | Dowell et al. |
| 6,214,017 | B1 |  | 4/2001  | Stoddard et al. |
| 6,537,291 | B2 | * | 3/2003 | Friedman et al. ............. 606/169 |
| 6,653,760 | B1 | * | 11/2003 | Goodson ....................... 310/325 |
| 6,875,220 | B2 | * | 4/2005  | Du et al. ....................... 606/169 |
| 2002/0010486 | A1 | * | 1/2002 | Hirt ............................... 606/169 |
| 2002/0165470 | A1 | * | 11/2002 | Pal et al. .......................... 601/2 |

OTHER PUBLICATIONS

International Search Report dated Sep. 28, 2004 for Application No. PCT/US03/39218.

* cited by examiner

*Primary Examiner* — Melanie Tyson
(74) *Attorney, Agent, or Firm* — Ulmer & Berne, LLP

(57) ABSTRACT

A percutaneous surgical instrument for de-bulking calculi or drilling bone includes an actuator for generating vibrations at ultrasonic frequencies and a horn coupled to said actuator for amplifying the actuator vibration. A fixed probe is attached to said horn for engaging the calculi and introducing the ultrasonic frequencies thereto. A floating probe is disposed concentric to and under said fixed probe and slidable thereover. A free mass is disposed between the horn and the floating probe for oscillating therebetween, in response to actuator vibration, for causing low frequency impact with the calculi.

7 Claims, 3 Drawing Sheets

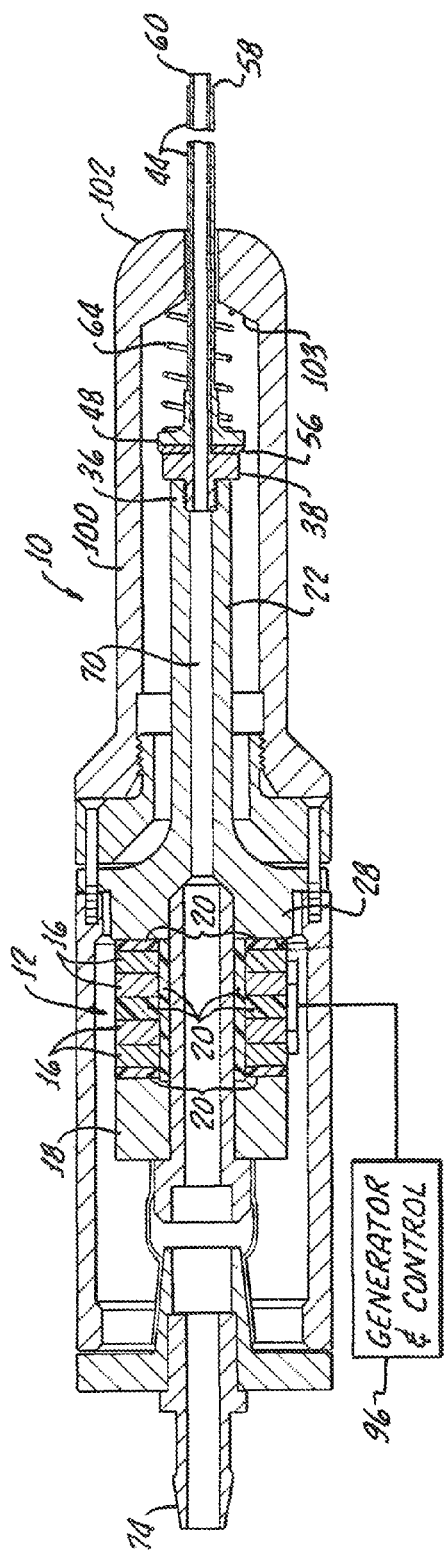

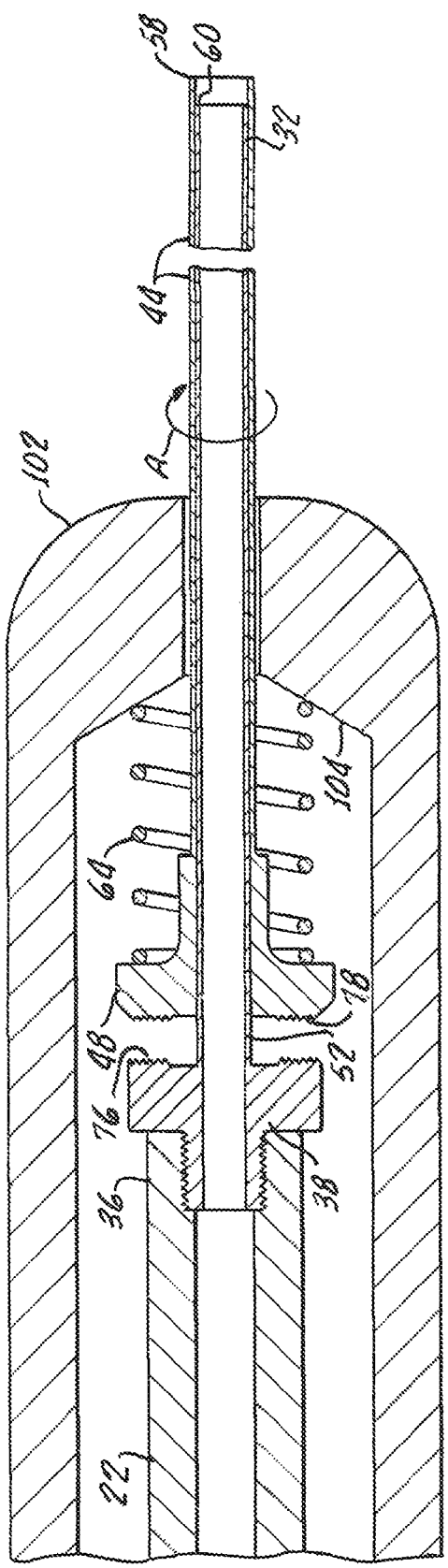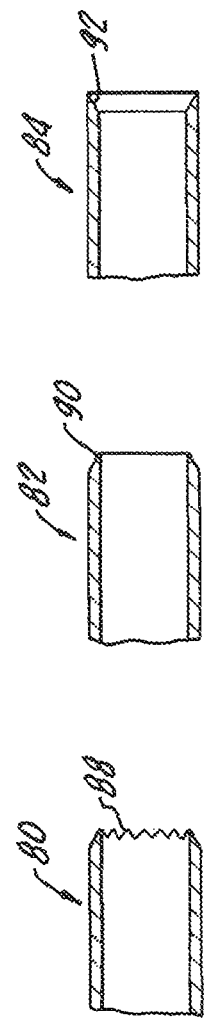

DUAL PROBE WITH FLOATING INNER PROBE

The present application is a continuation-in-part of U.S. Ser. No. 10/334,486 filed Dec. 30, 2002, now U.S. Pat. No. 6,875,220. This cited patent is to be incorporated in toto into the present application by this specific reference thereto.

The present invention is generally directed to a surgical instrument for disintegrating and de-bulking calculi or drilling stone, or bone and is more particularly directed to percutaneous surgical instruments for use in urological lithotripsy.

Many people develop calculi within their common bile, urinary, renal, or urethral systems. Such calculi may block ducts and/or cause great pain and therefore must be removed.

Originally, open surgery has been performed wherein multiple incisions are made to approach and remove the calculi. However, this treatment results in a relatively long recovery period and has long fallen into disfavor.

Presently, such calculi are destroyed in situ after which the fragmented calculi can be naturally evacuated. Various methods of de-bulking such calculi are known in the art. Instruments currently in use are typically ultrasonic fixed probe devices or pneumatic impacting probes that operate at fixed low frequencies.

Fixed ultrasonic probe devices that operate in the low 20-30 kHz range are best in disintegrating the small stones and pneumatic impact probes that deliver very high energy but at lower frequencies of 5-20 impacts per second are best for debulking large stones.

Another technique uses extra-corporeal shock waves for de-bulking calculi. In this instance, a patient is subjected to shock waves with the shock waves passing through a patient's skin which may cause bruising and is not acceptable for pregnant women and is slow, thus requiring multiple procedures for large stones. However, there are calculi, which cannot be removed by this technique because of the location, volume or composition, or health of patient.

The present invention is directed to a dual probe instrument that combines ultrasonic frequencies such as 20 kHz or more and high energy shock impacting of the low, for example, less than 1 kHz, frequencies. With the use of concentric probes, a lumen may be established therethrough allowing suction to remove calculi, or stone, debris from a patient.

SUMMARY OF THE INVENTION

A percutaneous surgical instrument for de-bulking calculi or drilling bone in accordance with the present invention generally includes an actuator for generating vibrations at ultrasonic frequencies along with a horn coupled to the actuator for amplifying the actuator vibration.

A fixed probe is attached to the horn for engaging the calculi and introducing ultrasonic frequencies thereto.

A floating probe is provided and disposed concentric to and over the fixed probe with the floating probe being slidable over the fixed probe. A free mass is disposed between the horn and floating probe for oscillating therebetween in response to actuator vibration for causing low frequency impact with the floating probe and calculi. The floating probe could also be on the inside and concentric to the fixed probe on the outside.

A generator may be provided for driving the actuator at desired power levels, frequencies, pulse cycles, and duty cycles in order to both change the ultrasonic frequency introduced by the fixed probe and the oscillations of the low frequency impacts.

In addition, the fixed probe may include a lumen therethrough for aspiration of disintegrated calculi or bone with the fix probe lumen in communication with a lumen through the horn.

The floating probe may be shorter or longer than the fixed probe and when shorter extends beyond a distal length of the fixed probe during oscillation of the floating probe.

A collar may be provided and fixed to the floating probe at a proximal end thereof for receiving impacts from the free mass. In addition, a housing may be provided for containing the actuator within the housing, including a distal end surrounding the fixed probe and the floating probe at a spaced apart distance from distal ends of the fixed probe and the floating probe.

A biasing spring element is preferably disposed between the collar and the housing distal end for urging the collar into the free mass, compression of the spring occurring during oscillation of the free mass.

The fixed probe and the floating probe may be detachable from the horn and further a plurality of fixed probes and floating probes may be utilized. The plurality of fixed and floating probe preferably include different cutting tips of different design and the generator driving frequency, pulse cycle and duty cycle is preferably selected to optimize the cutting/disintegration effectiveness of a selected fixed and floating probe. Additionally, varying spring rates will affect the impact energy and cycle frequency.

BRIEF DESCRIPTION OF THE DRAWINGS

The advantages and features of the present invention will be better understood by the following description when considered in conjunction with the accompanying drawings, in which:

FIG. 1 is a cross sectional view of a percutaneous surgical instrument in accordance with the present invention generally showing an actuator for generating vibrations at ultrasonic frequencies, a horn coupled to the actuator for amplifying the actuator vibration, a fixed probe attached to the horn for engaging calculi (not shown), a floating probe disposed concentric to and over the fixed probe, a free mass disposed between the fixed probe and the floating probe for oscillating therebetween and a generator/control for driving the actuator at desired frequencies;

FIG. 2 is an enlarged view of the distal end of the instrument shown in FIG. 1 showing the floating probe in a rearward position exposing a tip of the fixed probe;

FIG. 3 is a cross sectional view similar to FIG. 2 showing the floating probe in a forward position as moved by the free mass against a spring or spring like material with the tip of the floating probe past the tip of the fixed probe;

FIGS. 4a, b, c are enlarged cross sectional views of the tips of the fixed and floating probes showing various configurations for different cutting and disintegration procedures.

DETAILED DESCRIPTION

Figure 5:
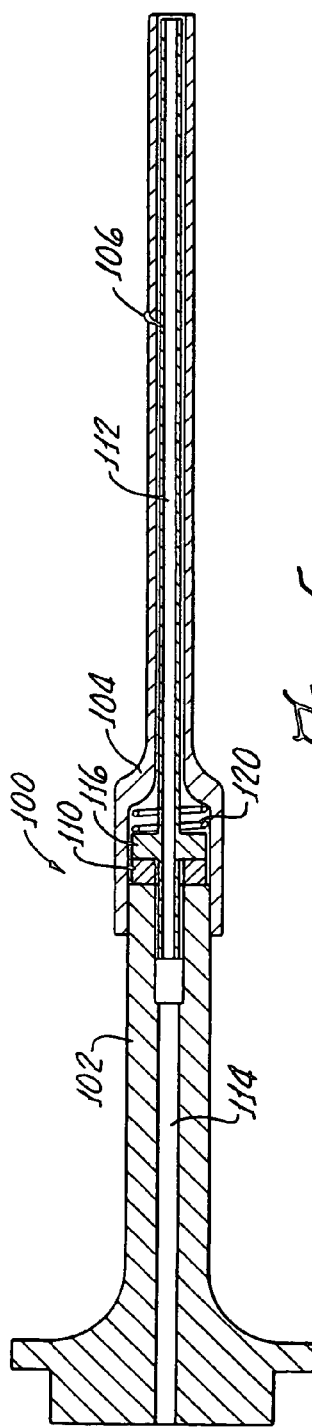
FIG. 5 is a cross sectional view of an alternative embodiment of a percutaneous surgical instrument in accordance with the present invention generally showing a horn; a fixed probe attached to the horn for engaging calculi (not shown), a floating probe disposed concentric to and within the fixed probe, and a free mass disposed between the horn and the floating probe for oscillating therebetween.

With reference to FIGS. 1-4c there is shown a percutaneous surgical instrument 10 for de-bulking calculi or drilling/coring bone generally including an actuator 12 for generating vibrations at ultrasonic frequencies which may be formed from a plurality of piezoelectric crystals or magnetostrictive assembly 16 and a back plate 18.

Additionally, a transducer assembly 16 may be configured reduce the capacitive effect of piezo crystals in an insulated stack. This may have an interference affect on other sensitive electrical instruments being operated close by. This is overcome with the placement of alumina insulators 20 at each end and one in the center of the poled crystals 16 to create opposite polarity.

A horn 22 is coupled to the actuator 12 at a proximal end 28 of the horn 22. This arrangement provides for amplification of the actuator 12 vibration.

A fixed probe 32 is attached to a distal end 36 of the horn 22 through a fitting 38 for receiving ultrasonic frequencies and engaging a calculi, not shown, for introducing the ultrasonic frequencies thereto.

As hereinabove noted, the fixed probe and actuator operate generally at ultrasonic frequencies of 18 kHz or above for disintegrating small stones, or calculi.

A floating probe 44 may be disposed concentric to and either over or under the fixed probe 32 and is slidable over the fixed probe 32.

The fixed and floating probes that may be coated with a lubricating element such as Teflon or a hydrophilic coating.

A collar 48 is attached to a proximal end 52 of the floating probe 44 and provides a means for receiving impacts from a free mass 56 which is disposed between the horn 22 and the floating probe 44 for oscillating therebetween in response to actuator 12 vibration. This causes low frequency impact with the floating probe 32 which in turn transfers the impact forces to the calculi as the distal end 58 of the floating probe 44 is driven past the distal end 60 of the fixed probe 32.

The induced movement of the free mass due to vibration of the horn 22 causes forward movement of the free mass 56 against a bias provided by a spring 64. The spring 64 returns the free mass 56 to an original position abutting the distal end 36 of the horn 22. These oscillations are at very low frequencies, for example, less than 1 kHz.

Accordingly, the floating probe 44 operating at these low frequencies efficiently breaks large stones into small pieces and the ultrasonically driven fixed probe 32 then is effective for disintegrating the ruptured calculi into finer particles which then may be aspirated through a lumen through the fixed probe 32 and a lumen 70 through the horn 22 which communicates with a suction port 74 interconnected with a vacuum source (not shown).

Rotation of the floating probe (as indicated by the arrow A in FIG. 3) may be effected through the use of contoured engagement surfaces 76, 78 on the fitting 38 and floating probe collar 48.

It should be appreciated that the fixed probe 32 and the floating probe 44 shown represent a plurality of fixed and floating probes which may have a variety of tips 80, 82, 84 which may include saw or serrated teeth 88, external bevels 90 or internal bevels 92. Tip 85 is a floating tip that may have the cutting edge finished as 88, 90, or 92. The tips 80, 82, 84 provide examples of various configurations suitable for cutting or drilling calculi, flesh, or bone of different density and configuration.

The fixed probe 32 and the floating probe 44 are preferably adapted for interchangement with the horn 22 either by threading, as illustrated, or through any other conventional coupling arrangement such as press fitting, silver solder, or welding.

The fixed probe 32 and floating probe 44 may be made of various materials including grades of plastic. The outside diameter of the floating probe may be 4 mm and for use in lithotripsy, the distal end 58 outside floating probe 44 may be approximately 0-1 mm shorter than the distal end 60 of the fixed probe 32 and will extend past the fixed probe 32 longitudinally when excited as hereinabove noted.

A generator/controller 96 is provided for driving the actuator 12 at desired frequencies. The generator provides for varying the pulse frequencies to fit the type and size of stone or other material to assure the most expedient and efficient disintegration. In fact, the actuator 12 is driven at various power levels, frequencies, pulse cycles, and duty cycles to maximize efficiency of the instrument 10.

The actuator 12 may be driven by the generator 96 at various power levels, frequencies, pulse cycle frequency, and duty cycles to maximize the efficiency of each of the cutting tips 80, 82, 84, for example.

Preferably, the generator/controller 96 utilizes direct digital synthesis for frequency control.

A housing 100 is provided for containing the actuator 12 and it includes a distal end 102 surrounding the fixed probe 32 and floating probe 44. The housing distal end 100 is spaced apart from the distal ends 60, 58 of the fixed and floating probes 32 and 44. An interior surface 103 provides a means of support for the spring 64 which provides for the force to reposition the free mass 56 between the collar 48 and the housing distal end 102 as hereinabove noted.

Figure 6:
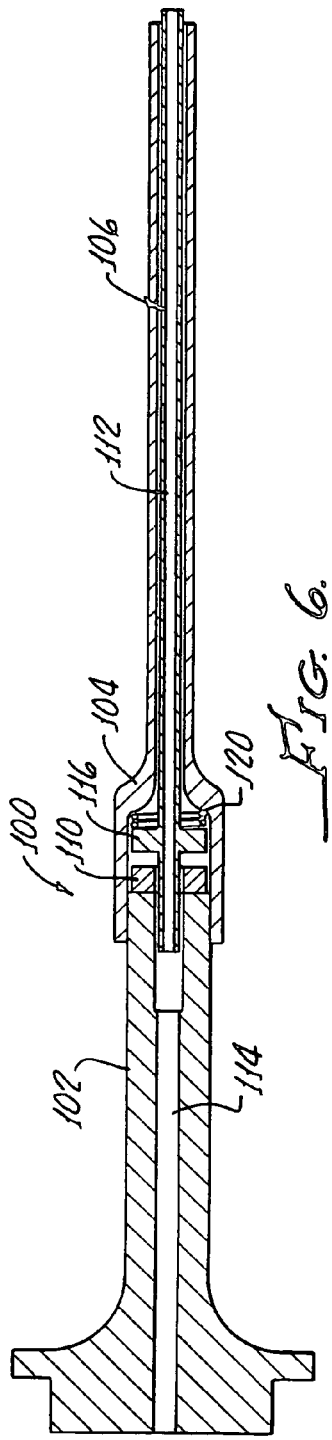
FIG. 6 is a cross sectional view similar to FIG. 5 showing the floating probe in a forward position as moved by the free mass against a spring or spring like material with the tip of the floating probe past the tip of the fixed probe.

With reference now to FIGS. 5 and 6 there is shown an alternative embodiment 100 in accordance with the present invention generally showing a horn 102 for coupling with the actuator 12, as shown in FIG. 1. In this embodiment, an outer probe 104 is fixed to the horn 102 and an inner floating probe 106 is disposed concentric to and under the fixed probe 104, the floating probe 106 being slidable along the fixed probe 104.

A free mass 110 is disposed between the horn 102 and the floating probe 106 for oscillating therebetween. A floating probe lumen 112 communicates with a horn lumen 114 for aspiration as hereinbefore described.

A collar fixed to the inner floating probe 116 is provided at a proximal end thereof for receiving impacts from the free mass 110 and a spring 120, or biasing element, is disposed between the collar 116 and a fixed probe 104 for retaining the free mass 110 to an original position. Operation of the instrument 100 is similar to that hereinbefore described in connection with the instrument 10.

Figure 7:
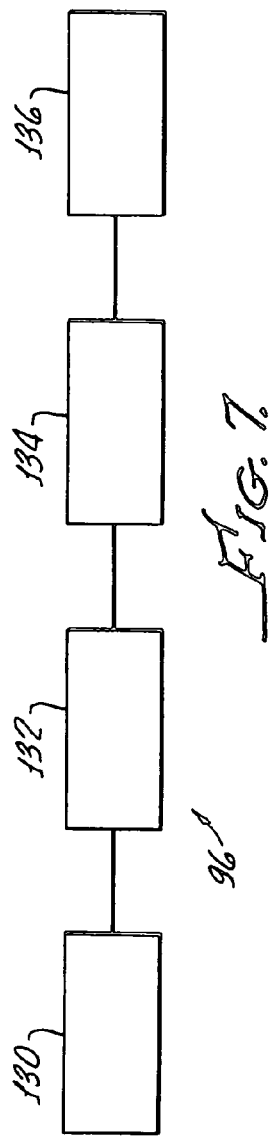
FIG. 7 is a block design of the generating/control.

With reference to FIG. 7, the generator 96 generally includes: a DC power source 130, a control module 132, a drive module 134, and an optional regulator module 136.

The DC power source 130 is the main power to power up the whole system. It is preferably a medical grade AC to DC power supply.

The control module 132 includes a microprocessor. The digital realization of tuning and frequency control is programmed to the microprocessor. The details are described in following sections.

The drive module 134 is a power amplifier. It amplifies the drive signal generated from the control module 132. A suitable Class D amplifier (or bridge inverter) may be used.

The regulator module, or board, is used if the output power level needs to be adjusted. PWM technique is applied to regulate the output of the DC power source to a desirable level.

Using Direct Digital Synthesis for Frequency Control

Frequency control in ultrasonic application means finding resonant frequency, keeping the system in or close to resonant frequency, or sweeping around resonant frequency.

Direct digital Synthesis (DDS), as used herein, is a technique for using digital data processing blocks to generate a frequency and phase tunable output signal referenced to a fixed precision clock source. The reference clock frequency is divided by the scaling factor set in a programmable binary tuning word. A complete DDS integrates a high speed and high performance D/A converter on a single chip. This is an attractive alternative to an analog based PLL synthesizer. In ultrasonic application, the DDS can provide distinct advantages over a traditional PLL circuit employed heretofore in an ultrasonic generator.

These advantages include:

1. DDS digital architecture eliminates the need for manual system tuning and "tweaking" typically associated with component aging and temperature drift in analog synthesizer solutions.

2. The digital control interface of DDS architecture allows a system to be optimized with sweep and pulse techniques remotely controlled.

3. Broad frequency range, hertz tuning resolution of the output frequency, and phase tuning capability ensures that the system can follow resonant frequency change associated with temperature, load, and other environmental changes. This also allows using one generator to drive different type of transducer. In other words, the generator can be a multiple device driver.

4. Fast "hopping speed" in tuning output frequency eliminates undesirable frequency under/overshoot or analog-related loop setting time.

5. In digital frequency control systems, digital filters can be implemented for feedback measurement instead of heretofore required complicated analog filters.

Optimized Tuning Algorithm

It is well known in the art that transducers have their lowest impedance at their resonant frequency, hence highest current occurs. This implies that it is possible to tune transducers to a frequency wherein the greatest current occurs. A method for searching for the system resonant frequency includes activating the transducer with different frequency signals and measuring the current flow. The frequency that producing maximum current is the resonant frequency or a frequency close to the resonant frequency.

Underlying Principle of Optimal Tuning Method

There is a fundamental underlying structure for most optimal algorithms. One starts at an initial point, determines, according to a fixed rule, a direction of movement; and then moves in that direction to an extremum of the objective function on that line. At the new point, a new direction is determined and the process is repeated. The primary differences between algorithms rest with the rule by which successive directions of movement are selected. Once the selection made, all algorithms call for movement to the extremum point on the corresponding line.

Most transducers have only one significant peak current near a resonant point. It can be safely assumed that the function being searched is unimodal and thus possesses a certain degree of smoothness. Accordingly, it is to be expected that more efficient search techniques exploiting this smoothness can be devised. Techniques of this nature are usually based on curve fitting procedures where a smooth curve is passed through the previously measured points in order to estimate of extremum point. Since there is no real time measurements of derivatives, quadratic fit is applied here.

Give $x_1$, $x_2$, $x_3$ and corresponding measurements $y_1$, $y_2$, $y_3$, we construct the quadratic passing through these points, $$q(x) = \sum_{i=1}^{3} y_i \frac{\prod_{j \neq i}(x - x_i)}{\prod_{j \neq i}(x_i - x_j)}$$

and determine a new point $x_4$ as the point where the derivative of q vanishes. Thus $$x_4 = \frac{1}{2} \frac{b_{23}y_1 + b_{31}y_2 + b_{12}y_3}{a_{23}y_1 + a_{31}y_2 + a_{12}y_3} \quad (1)$$

where $a_{ij}=x_i-x_j$, $b_{ij}=x_i^2-x_j^2$

If, however, we apply this technique directly, there is the possibility that the process would diverge or wander about meaningless. In other words, the process may never get close enough to the solution. For application here the key to guaranteeing converge is to find three points, such that a quadratic fit these points will have a maximum.

It is know that the current through transducer has a peak at resonant frequency. We can initiate our search procedure by searching along the line until we find three points $x_1$, $x_2$, $x_3$ with $x_1<x_2<x_3$ such that $y_1 \leq y_2 \geq y_3$. This pattern will have a maximum and the maximum point will lie in the interval $[x_1,x_3]$. The way to find such sequence points will be discussed in next section.

Real-Time Implementation

It has been discussed in last section, to ensure the search converge to resonant point, it is necessary to find three point $f_1$, $f_0$, $f_2$ that satisfied:

$v(f_1) \leq v(f_0) \geq v(f_2)$ where $v(f_1)$, $v(f_0)$, $v(f_2)$, are the measurements at frequency equal to $f_1$, $f_0$, $f_2$ respectively.

Assuming that we know the resonant point is in $[f_1,f_2]$, we can start at any frequency $f_0$, through a series of halvings and doublings of $f_0$ and comparing the corresponding $v(f_0)$ with $v(f_1)$ and $v(f_2)$, a three-point pattern can be determined.

In practice, it is possible to calculate the resonant frequency according to the mechanical characteristics of a transducer. We can initial $f_0$ equals the calculated resonant frequency, then let $f_1=f_0-\Delta f$ $f_2=f_0+\Delta f$ $\Delta f$ should be chosen as small as possible as long as the three point pattern still exists. In other words, the narrower the bandwidth, the smaller $\Delta f$ is. In the present dual probe application $\Delta f$ is 200. To avoid staying at a local maximum, the other two points at $f_0-2\Delta f$ and $f_0+2\Delta f$ are also compared to at $f_0$.

Resonant Frequency Follower

It is well known in the art that the resonant frequency of the transducer is due to load or environment change. To keep a transducer working at resonant frequency, it is necessary to have a returning procedure. Since the resonant frequency only changes in a relative small range and the change is relatively slow, it may not necessary to go through the entire tuning process each time. Once the transducer is tuned, we can only compare three points at $f_0$, $f_0-\Delta f$ and $f_0+\Delta f$. Then the frequency at which the current is largest will be the new operating frequency. $\Delta f$ depends on the bandwidth of the transducer. The time between two tuning procedures is dependent on working conditions and characteristics of transducer. This resonant frequency follower can be use for the application where the resonant frequency has large thermal drift.

Pulse on Pulse

Generally the electrical system is faster than the transducer utilized and the transducer is faster than the mechanical system (including the floating probe 44). If one analyzes the system in different time scale, a step input to electrical system can be treated as impulse for a transducer mechanical system, while a step input for a transducer could only be an impulse input for the entire mechanical system. By introducing pulse on pulse, one can get pseudo impulse response of a mechanical system. In some application, this can generate an impact force like a hammer.

In a digital system, different time scale means different sampling frequency. This pulse on pulse system is a different interrupt period.

Nonlinear Sweep and Random Disturbance

If one looks at the system in frequency domain, the system is a rotor vector with changing amplitude. The conventional linear sweep is driving the vector with triangle input using the resonant frequency as neutral point.

Some transducers have larger frequency bandwidth than others. Some transducers have more than one resonant frequency in a small frequency range. Thus, a nonlinear sweep may be necessary. An input waveform can be developed according to mechanical characteristics of the transducer and experiments, such that a more desirable vibration mode may be obtained and undesirable vibration modes minimized.

To implement sweep to a digital system, it is safe to say that the sweep frequency is always slower than the drive frequency. Thus, the drive frequency can always be used as a carrier. A frequency modulation can be developed.

In some cases, the system needs some level of disturbance. Accordingly, random frequency change in certain ranges can be implemented in accordance with the present invention.

Although there has been hereinabove described a specific dual probe and method in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A percutaneous surgical instrument comprising:
   an actuator for generating vibrations at ultrasonic frequencies;
   a horn coupled to said actuator for amplifying the actuator vibration;
   an ultrasonically driven fixed probe attached to said horn, said fixed probe having an end for engaging calculi and introducing the ultrasonic frequencies thereto;
   an ultrasonically driven floating probe disposed concentric to and under said fixed probe, said floating probe being slidable along said fixed probe and having an end for simultaneously introducing ultrasonically driven low-frequency impact with the calculi;
   an ultrasonically driven free mass, disposed between said horn and said floating probe for oscillating therebetween, in response to actuator ultrasonic vibration, for causing ultrasonically driven low frequency impact with the floating probe which, in turn, introduces the low frequency impact with the calculi;
   a collar for receiving impacts from said free mass, said collar coupled to said floating probe at a proximal end thereof, said collar being disposed internal to a proximal end of said fixed probe and being slidable along said fixed probe; and
   a generator for driving said actuator at desired power levels, frequencies, pulse cycles and duty cycles in order to both provide the ultrasonic frequency introduced by said fixed probe and the oscillations of the low frequency impacts.

2. The instrument according to claim 1 wherein said floating probe includes a lumen therethrough for aspiration of disintegrated calculi.

3. The instrument according to claim 2 wherein said horn includes a lumen therethrough in communication with the floating probe lumen.

4. The instrument according to claim 1 wherein said floating probe extends beyond a distal end of said fixed probe during oscillation of said floating probe.

5. The instrument according to claim 1 further comprising a biasing element disposed between said collar and a housing of the percutaneous surgical instrument.

6. The instrument according to claim 1 wherein said actuator includes a transducer assembly having a stack of piezo crystals configured to reduce a capacitive effect of the piezo crystals.

7. The instrument according to claim 6 wherein said actuator is configured with alumina insulators disposed in the stack of piezo crystals.

* * * * *